(12) United States Patent
Wettstein et al.

(10) Patent No.: US 11,504,380 B2
(45) Date of Patent: Nov. 22, 2022

(54) METHOD OF TREATMENT OF CIRRHOSIS

(71) Applicant: INVENTIVA, Daix (FR)

(72) Inventors: Guillaume Wettstein, Daix (FR); Pierre Broqua, Daix (FR); Jean-Louis Junien, Paris (FR)

(73) Assignee: INVENTIVA, Daix (FR)

( * ) Notice: Subject to any disclaimer, the term of this patent is extended or adjusted under 35 U.S.C. 154(b) by 0 days.

(21) Appl. No.: 16/677,756

(22) Filed: Nov. 8, 2019

(65) Prior Publication Data

US 2021/0137937 A1 May 13, 2021

(51) Int. Cl.
*A61K 31/54* (2006.01)
*A61K 31/5415* (2006.01)
*A61P 1/16* (2006.01)

(52) U.S. Cl.
CPC ............ *A61K 31/5415* (2013.01); *A61P 1/16* (2018.01)

(58) Field of Classification Search
CPC ............................... A61K 31/428; A61P 1/16
USPC ......................................................... 514/367
See application file for complete search history.

(56) References Cited

U.S. PATENT DOCUMENTS

| | | |
|---|---|---|
| 7,795,297 B2 | 9/2010 | Binet et al. |
| 10,052,311 B2 | 8/2018 | Konstantinova et al. |
| 10,383,858 B2 | 8/2019 | Konstantinova et al. |

OTHER PUBLICATIONS

Suk et al. "Staging of liver fibrosis or cirrhosis: the role of hepatic venous pressure gradient measurement," World Journal of Hepatology, 2015, vol. 7, No. 3, pp. 607-615. (Year: 2015).*
Verheist et al. "Cirrhosis: Reviewing the literature and future perspectives," European Medical Journal, 2016, pp. 111-117 (Year: 2016).*
Kaur et al. "Deuteration as a tool for optimization of metabolic stability and toxicity of drugs," Global J. Pharmacy & Pharmaceutical Science, 2017, vol. 1, No. 4, pp. 1-11 (Year: 2017).*
Tsai et al. "Beneficial effects of the peroxisome proliferator-activated receptor α/γ agonist aleglitazar on progressive hepatic and splanchnic abnormalities in Cirrhotic rats with portal hypertension" The American J. Pathology, Jul. 2018, vol. 188, pp. 1608-1624 (Year: 2018).*
G. D'Amico et al., "Clinical states of cirrhosis and competing risks", Journal of Hepatology, 2018; 68:563-576.
M. Martinez-Esparza et al., "Imflammatory status in human hepatic cirrhosis", World Journal of Gastroenterology, 2015; 21(41):11522-11541.
M. Dirchwolf et al., "Role of systematic . . . pathogenesis to prognosis", World Journal of Hepatology, 2015;7(16): 1974-1981.
Zhou et al., "Pathogenesis of liver cirrhosis", World Journal of Gastroenterology, 2014; 20:7312-7324.
J. Poisson et al., "Liver sinusoidal endothelial . . . in liver diseases", Journal of Hepatology, 2017, 66, 212-227.
L. Turco et al., "Portal Hypertension Pathogenesis and Diagnosis", Clin Liver Dis 23 (2019), 573-587.
P. Lefebvre et al., "Sorting out the roles . . . and vascular homeostasis", Journal of Clinical Investigation, 2006; 116:571-580.

(Continued)

*Primary Examiner* — Shengjun Wang
(74) *Attorney, Agent, or Firm* — Clark & Brody LP

(57) ABSTRACT

The invention relates to a method of treating cirrhosis which comprises administering to a subject in need thereof lanifibranor or a deuterated derivative thereof.

7 Claims, 5 Drawing Sheets

(56) References Cited

OTHER PUBLICATIONS

A. Zambon et al., "Modulation of Hepatic . . . by PPAR-α Activators", Arterioscler Thromb Vasc Biol 2006; 26:977-986.
Lee et al., "PPARδ regulates glucose metabolism and insulin sensitivity", Proc Natl Acad Sci USA 2006; 103:3444-3449.
T. Adhikary et al., "The transcriptional PPARβ/δ . . . agonist-induced activation state", Nucleic Acids Research, 2015, vol. 43, No. 10, 5033-5051.
B. Grygiel-Gorniak, "Peroxisome proliferator-activated . . . clinical implications—a review", Nutrition Journal, 2014; 13:17.
S. Hazra et al., "Peroxisome Proliferartor-activated . . . Hepatic Stellate Cells", The Journal of Biological Chemistry, 2004; 279:11392-11401.
F. Marra et al., "Ligands of Peroxisome . . . Hepatic Stellate Cells", Gastroenterology 2000; 119:466-478.
Tsai et al., "Beneficial Effects of the . . . with Portal Hypertension" The American Journal of Pathology, 2018; 188:1608-1624.
Y. Liu et al., "The Role of PPAR-δ . . . Critical Transcription Factor" International Journal of Molecular Sciences, 2018; 19: 3339.

\* cited by examiner

Fig.3a
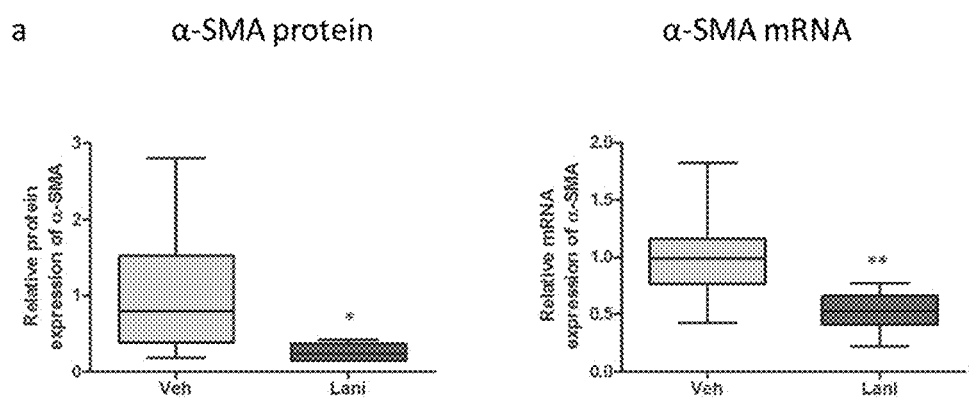
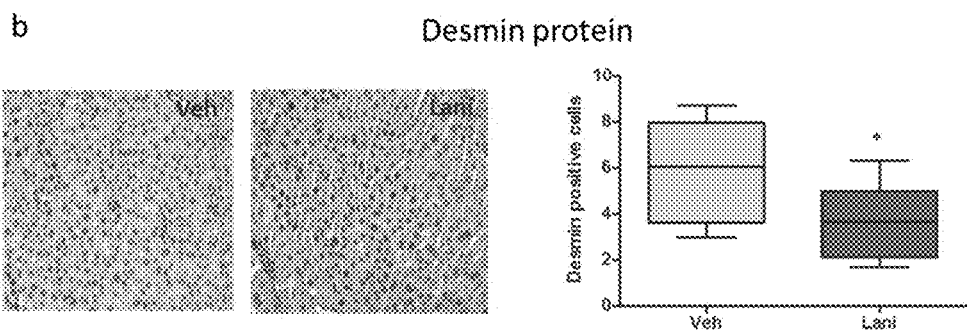
Fig.3b

METHOD OF TREATMENT OF CIRRHOSIS

FIELD OF THE INVENTION

The present invention relates to a method of treatment of cirrhosis which comprises administering to a subject in need thereof lanifibranor or a deuterated derivative thereof, or a pharmaceutically acceptable salt thereof.

BACKGROUND OF THE INVENTION

Cirrhosis is the resultant of liver damage inducing necro-inflammation leading to the development of scar tissue and liver fibrosis. The primary injuries could arise from many forms of liver diseases and conditions, such as e.g. chronic alcoholism, chronic viral hepatitis (hepatitis B, C and D), fat accumulating in the liver (nonalcoholic fatty liver disease), iron buildup in the body (hemochromatosis), copper accumulated in the liver (Wilson's disease), poorly formed bile ducts (biliary atresia), primary biliary cirrhosis (PBC), primary sclerosing cholangitis (PSC) or medications, including methotrexate or isoniazid (see http://www.mayoclinic.org/diseases-conditions/cirrhosis/symptoms-causes/syc-20351487).

Although various events could lead to the development of cirrhosis, the physiopathology remains similar with inflammation, parenchymal necrosis, fibrosis, vascular impairment and loss of liver function being the main features (1). Compensated cirrhosis remains asymptomatic despite the numerous intrahepatic impairments until its decompensation identified according to the presence of bleeding varices, ascites and jaundice.

Systemic inflammation is one of the key element of cirrhosis physiopathology. The inflammatory reaction is the coordinated process by which the liver responds to local insults trying to restore the original structure and hepatic function. However if the insults or damages are persistent, the maintained inflammation gives rise to a gradual replacement of normal hepatic tissue by nonfunctional scar tissue (2). Systemic inflammation is mediated through the activation of all the innate and adaptative immune cells. This activation results in an increase in pro-inflammatory cytokines (ie: IL-6, IL-1β, IFNγ) and expression of cell activated markers (ie: ICAM-1, VCAM-1) (3). Hepatic Stellate Cells (HSC) plays an important role in immunology through its vitamin A storage role when quiescent and through its capacity to secretes many pro-inflammatory cytokines and chemokines when activated leading to immune cells recruitment within the liver Liver sinusoidal endothelial cells (LSEC) play also an important role in inflammation development through their expression of membrane markers allowing the immune cells to bind the LSEC and to enter the parenchymal liver. Of the different immune cells the macrophages are the main driver of inflammation through their abilities to further enhance inflammation. Dysregulation of the M1 (classical)/M2(alternative) macrophage polarized balance becomes apparent as a central mechanism implicated in the pathogenesis of chronic inflammatory diseases. This suggests that strategies impairing M1 macrophage phenotype and/or enhancing the M2 macrophage polarization could protect against intensified inflammation and in this way they could limit tissue injury (2).

Progression of chronic liver disease of any cause contributes to changes in the hepatic sinusoids mostly due to phenotypic and functional alterations in hepatic stellate cells (HSC) and liver sinusoidal endothelial cells (LSEC).

LSEC are specialized endothelial cells localized at the interface between the blood derived from the gut and the adipose tissue on the one hand, and liver cells such as hepatocytes, Kuppfer cells and Stellate cells on the other hand. LSECs are for example major regulators of the bidirectional lipid exchange between the blood and the liver parenchyma. LSEC fenestrae allow for efficient transfer of lipoproteins, chylomicrons remnants and other macromolecules from the sinusoidal blood flow to the space of Disse where they are taken up by hepatocytes.

Hepatic stellate cells are nonparenchymal cells close to LSECs, in the space of Diss which stores retinoids in physiological conditions and shift their phenotype to an activated myofibroblastic state during liver injury and inflammation secreting large amount of extracellular matrix components and promoting liver fibrosis.

During chronic liver diseases functional alterations in LSEC and HSC are key elements of cirrhosis progression.

LSECs acquire a pro-inflammatory phenotype such as expression of inflammatory receptors (i.e., ICAM1, VCAM1) that favors the recruitment, adhesion and transmigration of blood leucocytes. In addition, the release of inflammatory mediators by LSEC contributes to the inflammatory response by activating neighboring Kuppfer cells, further enhancing intrahepatic inflammation. Finally macrophages located in the space of Disse and in the parenchyma respectively, will be activated by the inflammatory and profibrotic environment and further develop a deleterious environment (4).

LSECs also contribute to liver fibrosis through capillarization and endothelial dysfunction. Capillarization of LSEC is observed in patients and animal models of chronic liver disease and promotes the development of fibrosis. Healthy LSECs maintain HSC quiescence whereas capillarized LSECs lose this ability (5).

The main complication associated to cirrhosis that is responsible for moving from compensated stage to decompensated stage is portal hypertension.

Portal venous system drains blood from intestine, spleen, and pancreas into the liver mainly via the superior mesenteric, inferior mesenteric and splenic veins. The portal vein supplies the liver with 80% of its blood and 20% of its oxygen requirement. The portal venous system is a valve less system, so that pressure anywhere in the system is the same. The pressure in the portal venous system can rise either due to an obstruction in the extra hepatic portal venous system or due to increase in resistance to portal blood flow. In cirrhosis, the increase in portal pressure is caused by liver vascular resistance. Increased intrahepatic resistance results from a combination of: (i) structural alterations in the hepatic sinusoids (sinusoidal fibrosis and regenerative nodules) and (ii) functional (dynamic) vasoconstriction of the intrahepatic circulation resulting from a decreased production of vasodilators from sinusoid cells. HSC respond to liver injury by proliferation, transformation into contractile myofibroblasts, and extracellular matrix deposition in the hepatic sinusoids. LSEC which normally contain fenestrae respond to injury by losing fenestrae leading to capillarization of the sinusoids by deposition of basement membrane. Capillarization may act as a very early player both in increasing intrahepatic resistance and in promoting fibrosis formation. LSECs can also increase the contractility of sinusoid cells.

The increased intrahepatic vascular resistance leads to an increased pressure in the portal vein system, which induces shear stress in the splanchnic vessels and the release of vasodilators. Consequent splanchnic arterial vasodilation is the core factor in the progression and worsening of portal hypertension leading to the development of clinically significant portal hypertension. Splanchnic vasodilation also affects the systemic circulation leading to a decrease in mean arterial pressure. Increased pressure in the portal vein causes large veins (varices) to develop across the esophagus and stomach to get around the obstruction. The varices become fragile and can bleed easily. As cirrhosis progresses, more and more scar tissue forms, making it difficult for the liver to function leading to decompensated cirrhosis. Advanced cirrhosis is life-threatening, and may require liver transplant surgery (6). Lanifibranor {4-[1-(1,3-benzothiazol-6-ylsulfonyl)-5-chloroindol-2-yl]butanoic acid; CAS 927961-18-0} is a pan-PPAR agonist which is currently in clinical development for the treatment of patients with non-alcoholic steatohepatitis (NASH), for which there is currently no approved therapy. PPARs are ligand-activated transcription factors belonging to the nuclear hormone receptor family that regulate the expression of genes. There are three PPAR isoforms known as PPARα, PPARγ and PPARδ. PPARα is highly expressed in hepatocytes and controls fatty acid transport and β-oxidation and exerts anti-inflammatory properties (7,8). PPARδ regulates glucose and lipids metabolism as well as insulin resistance in the skeletal muscle (9). PARβ/δ serves as a receptor for a broad range of natural agonists with function in inflammatory processes, including unsaturated fatty acids and 15-hydroxyeicosatetraenoic acid (15-HETE) (10). PPARγ is highly expressed in adipose tissue where it promotes adipocyte differentiation, increases glucose uptake and triglyceride storage and secretion of anti-inflammatory cytokines (11). PPARγ is also expressed in the hepatic stellate cells (HSC) where it controls their fate and maintains them in a quiescent state preventing their activation, trans-differentiation into myofibroblasts and production of collagen and fibronectin, the major constituents of the fibrotic scar in the liver (12,13). The effects of aleglitazar, a dual α/γ PPAR agonist, in cirrhotic rats with portal hypertension, have been recently investigated (14).

While there are PPAR agonists that target only one or two PPAR isoforms for activation, lanifibranor activates all three PPAR isoforms (hence the reference to a "pan-PPAR agonist") in a moderately potent manner, with a well-balanced activation of PPARα and PPARδ, and a partial activation of PPARγ.

PPARδ is involved in liver inflammation through its role in promoting polarization to alternative M2 macrophages having less inflammatory potential relative to M1 macrophages (15). However the role of PPARδ in macrophages might be more complex and provides different effect on macrophages at different stages of NASH and cirrhosis development. Indeed PPARδ could control macrophages through canonical regulation involving DNA binding and genes regulation but also through endogenous ligand binding leading to the inhibition of multiple pro-inflammatory mediators (10).

It has now been found that lanifibranor exerts beneficial effects in a pre-clinical model of cirrhosis, improving the phenotype of liver sinusoidal endothelial cells, leading to marked amelioration in fibrosis, sinusoidal capillarization and portal hypertension. Accordingly, the use of lanifibranor is contemplated for the treatment of advanced chronic liver disease, notably cirrhosis.

SUMMARY OF THE INVENTION

The present invention relates to a method of treatment of advanced chronic liver disease, notably cirrhosis, which comprises administering to a subject in need thereof lanifibranor or a deuterated derivative thereof, or a pharmaceutically acceptable salt thereof, or a pharmaceutically acceptable solvate thereof.

The invention also relates to a method of regulating portal hypertension which comprises administering to a subject in need thereof lanifibranor or a deuterated derivative thereof, or a pharmaceutically acceptable salt thereof, or a pharmaceutically acceptable solvate thereof.

BRIEF DESCRIPTION OF THE DRAWINGS

FIG. 3a shows α-SMA levels in rats treated with vehicle or lanifibranor.

FIG. 3b shows Desmin levels in rats treated with vehicle or lanifibranor.

DETAILED DESCRIPTION OF THE INVENTION

Figure 1:
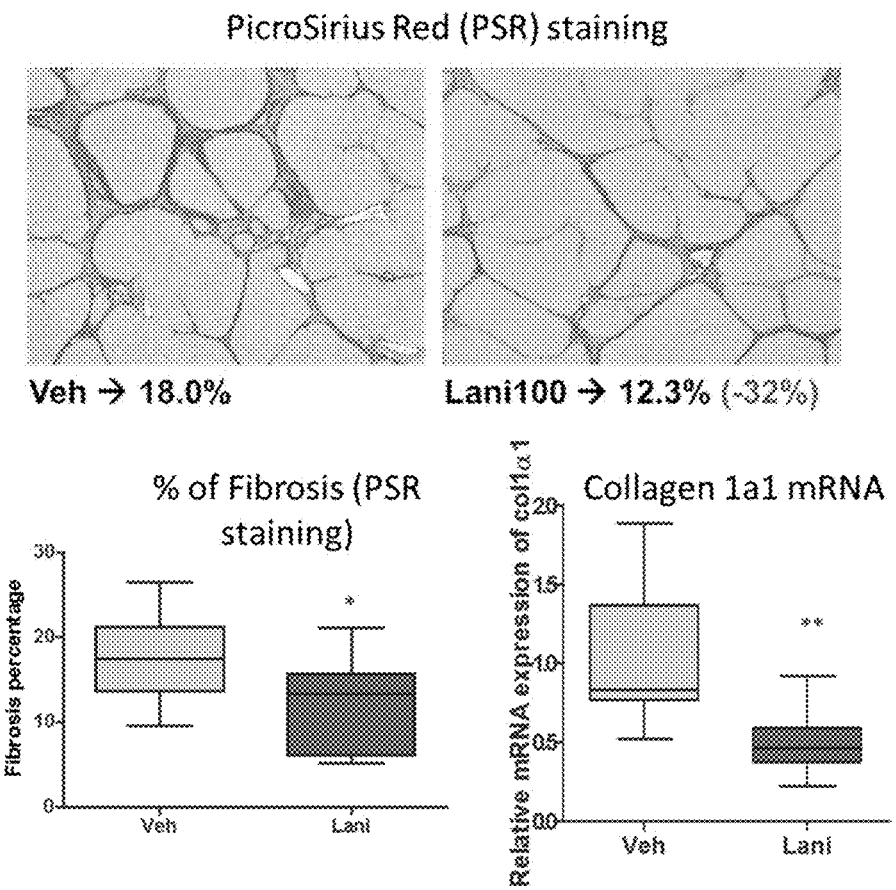
FIG. 1 shows the extent of fibrosis, as demonstrated by collagen deposition, in rats treated with vehicle or lanifibranor.

The invention relates to a method of treatment of advanced chronic liver disease which comprises administering to a subject in need thereof lanifibranor or a deuterated derivative thereof, or a pharmaceutically acceptable salt thereof, or a pharmaceutically acceptable solvate thereof.

In some embodiments, advanced chronic liver disease is cirrhosis. In some embodiments, cirrhosis is caused by alcohol use disorder, such as early stage alcoholism, chronic alcoholism or end-stage alcoholism. In other embodiments, cirrhosis is caused by chronic viral hepatitis. In other embodiments cirrhosis is caused by NAFLD and/or NASH. In other embodiments cirrhosis is caused by primary biliary cirrhosis and/or primary sclerosing cholangitis. In other embodiments cirrhosis is caused by medication.

In some embodiments, a deuterated derivative of lanifibranor is a compound of formula (I):

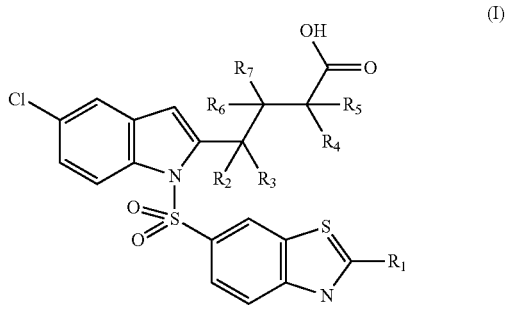

wherein at least one of the groups $R_1$ to $R_7$ is a deuterium (D) atom and the other groups $R_1$ to $R_7$ are hydrogen (H) atoms, as described in French patent application n° 18 57021. In some aspects, at least group $R_1$ is D. In some aspects at least one of the groups $R_2$ to $R_7$ is D, notably at least one of the groups $R_2$ and $R_3$ and/or at least one of the groups $R_4$ and $R_5$ and/or at least one of the groups $R_6$ and $R_7$ is D. In a preferred aspect each of $R_2$, $R_3$, $R_4$, $R_5$, $R_6$ and $R_7$ is D.

In some embodiments, a deuterated derivative of lanifibranor is 4-(1-(2-deuterio-1,3-benzothiazol-6-yl)sulfonyl)-5-chloro-1H-indol-2-yl)butanoic acid. In other embodiments a deuterated derivative of lanifibranor is 4-[1-(1,3-benzothiazol-6-ylsulfonyl)-5-chloro-indol-2-yl]-2,2,3,3,4,4-hexadeuteriobutanoic acid.

In some embodiments, lanifibranor or a deuterated derivative thereof is in the form of one of its pharmaceutically acceptable salts or solvates. The term 'solvate' is used herein to describe a molecular complex comprising lanifibranor or a deuterated derivative thereof and one or more pharmaceutically acceptable solvent molecules, for example, ethanol. The term 'hydrate' is employed when said solvent is water. Pharmaceutically acceptable salts of lanifibranor or a deuterated derivative thereof include the acid addition and base salts thereof. In some aspects, the salts of lanifibranor or a deuterated derivative thereof include those formed with a non-toxic, pharmaceutically acceptable organic or inorganic base. Examples of inorganic bases include sodium hydroxide, potassium hydroxide, magnesium hydroxide and calcium hydroxide. Examples of organic bases include amines, amino alcohols, basic amino acids such as lysine or arginine, and quaternary ammonium compounds such as betaine or choline.

The invention also relates to a method of regulating portal hypertension which comprises administering to a subject in need thereof lanifibranor or a deuterated derivative thereof (as defined above), or a pharmaceutically acceptable salt thereof, or a pharmaceutically acceptable solvate thereof.

Lanifibranor or a deuterated derivative thereof, or a pharmaceutically acceptable salt thereof or a pharmaceutically acceptable solvate thereof, can be formulated into a pharmaceutical composition comprising one or more pharmaceutically acceptable excipients. The choice of excipient(s) will to a large extent depend on factors such as the particular mode of administration, the effect of the excipient on solubility and stability, and the nature of the dosage form. Pharmaceutical compositions of the invention can be prepared by conventional methods, as described e.g. in Remington's Pharmaceutical Sciences, 19th Edition (Mack Publishing Company, 1995), incorporated herein by reference.

In some embodiments, the pharmaceutical composition is suitable for oral administration. Examples of compositions suitable for oral administration include: tablets, soft or hard (gelatin) capsules, lozenges, gels, syrups, or suspensions.

In some embodiments, the pharmaceutical composition comprises from about 1 to about 1000 mg of lanifibranor or deuterated derivative thereof, such as for example about 10 mg, about 20 mg, about 50 mg, about 100 mg, about 200 mg, about 500 mg, about 750 mg or about 1000 mg of said compound.

The invention is illustrated by the following example.

EXAMPLE

Lanifibranor has been assessed in a rat model of cirrhosis induced by the administration of thioacetamide (TAA), which administration leads to the development of fibrosis in the early time points and then of cirrhosis in the late time points, turning for the majority of the animals to decompensated cirrhosis.

Sprague Dawley rats (12-15 rats per groups) were intraperitoneally administered TAA (twice a week) for a period of twelve weeks to ensure reaching decompensated cirrhosis. At the end of this period, a TAA detoxification period of four days was observed. The rats were then orally administered for two weeks with either lanifibranor at 100 mg/kg/day in vehicle (methylcellulose 1%+poloxamer-188 0.1%), or with vehicle alone (control). At the end of the two weeks of treatment in vivo systemic and hepatic hemodynamics were determined and rats were then sacrificed, and plasma samples and liver tissue were harvested.

The hemodynamics measurements were obtained as follow: mean arterial pressure (MAP) and heart rate (HR) were measured by cannulating the femoral artery; portal pressure (PP) was measured by cannulating the ileocolic vein, both with a heparinized p50 catheter (Portex) connected to a pressure probe; portal blood flow (PBF) was determined with the help of specific non-constrictive perivascular ultrasonic transit-time flow probe (Transonic Systems Inc.).

Liver tissue samples for histology were fixed in 4% formaldehyde (Sigma), embedded in paraffin, sectioned and stained with 0.1% Sirius Red in picric acid aqueous solution (Sigma). Sinusoidal fenestrae were analyzed by electronic microscopy.

Triton lysis buffer was used for protein extraction of liver tissue samples. Proteins were separated by molecular weight by electrophoresis using a sodium dodecylsulphate polyacrylamide gel, and transferred to a nitrocellulose membrane (Western blot).

RNA was extracted from liver tissue using Trizol (Life Technologies), and quantified with the help of a NanoDrop spectrophotometer. Reverse transcription was carried out following QuantiTect reverse transcription kit (Qiagen). qPCR was performed using PowerUp SYBR Green Master Mix (Thermo Fisher) and specific primers.

Hemodynamic Parameters and Ascites

In TAA-exposed rats, lanifibranor at 100 mg/kg significantly reduced portal pressure (PP) (11.2±0.5 mmHg vs 13.1±0.4 mmHg, p<0.05), intrahepatic resistance (IHVR) (0.75±0.1 mmHg·min/mL vs 0.53±0.06 mmHg·min/mL, p<0.05) compared to vehicle. No change was observed regarding body weight, liver weight, spleen weight or heart rate as can be seen from Table 1. In TAA-exposed rats, lanifibranor at 100 mg/kg also significantly reduced ascites (16% Vs 67%; p=0.04) compared to vehicle (Table 1).

TABLE 1

|  | Vehicle | Lanifibranor | p-value |
| --- | --- | --- | --- |
| MAP (mmHg) | 81 ± 3 | 84 ± 2 | 0.4 |
| PP (mmHg) | 13.1 ± 0.4 | 11.2 ± 0.5 | 0.003 |
| PBF (mL/min) | 19.0 ± 1.7 | 23.5 ± 2.1 | 0.1 |
| IHVR (mmHg · min/mL) | 0.75 ± 0.1 | 0.53 ± 0.06 | 0.02 |
| Body weight (g) | 485 ± 18 | 484 ± 16 | >0.2 |
| Liver weight (g) | 14.4 ± 0.3 | 14.1 ± 0.7 | >0.2 |
| Spleen weight | 1.6 ± 0.1 | 1.3 ± 0.1 | 0.08 |
| HR (bpm) | 328 ± 6 | 334 ± 8 | >0.2 |
| Ascites (%) | 67 | 16 | 0.04 |

Fibrosis

In TAA-exposed rats, lanifibranor at 100 mg/kg significantly reduced established fibrosis as demonstrated by the histological decrease of 32% in collagen deposition (Picro-Sirius Red, PSR, staining 12.3% VS 18%, p<0.05) compared to vehicle. This histological observation was accompanied by a significant decrease in collagen 1a1 mRNA expression (p<0.005) (FIG. 1).

Fibrosis Markers

Figure 2:
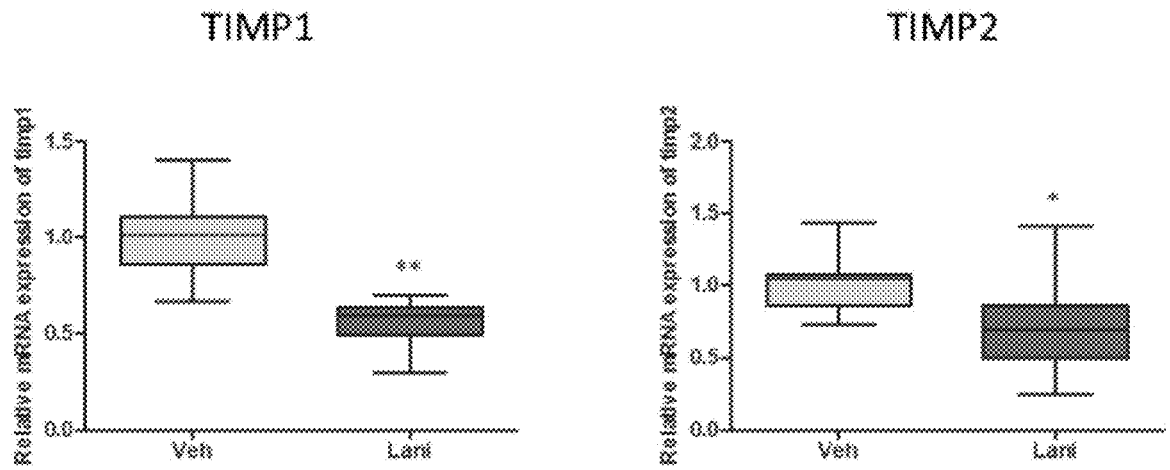
FIG. 2 shows TIMP1 and TIMP2 levels in rats treated with vehicle or lanifibranor.

In TAA-exposed rats, lanifibranor at 100 mg/kg significantly reduced TIMP1 and TIMP2 mRNA expression, two markers of fibrosis, (p<0.001 and p<0.05 respectively) compared to vehicle (FIG. 2).

Hepatic Stellate Cells (HSC) Activation

In TAA-exposed rats, lanifibranor at 100 mg/kg significantly reduced the expression of α-SMA (alpha-Smooth Muscle Actin), the main marker of HSC activation both at mRNA and protein level, compared to vehicle (p<0.005 and p<0.05 respectively) (FIG. 3a).

In TAA-exposed rats, lanifibranor at 100 mg/kg significantly reduced the protein level of Desmin (p<0.05) compared to vehicle (FIG. 3b)

Sinusoidal Capillarization

Figure 4:
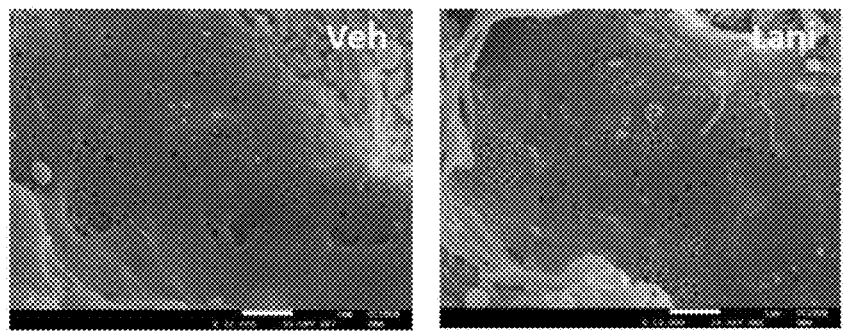
FIG. 4 shows the percentage of fenestrae in rats treated with vehicle or lanifibranor.
Figure 4:
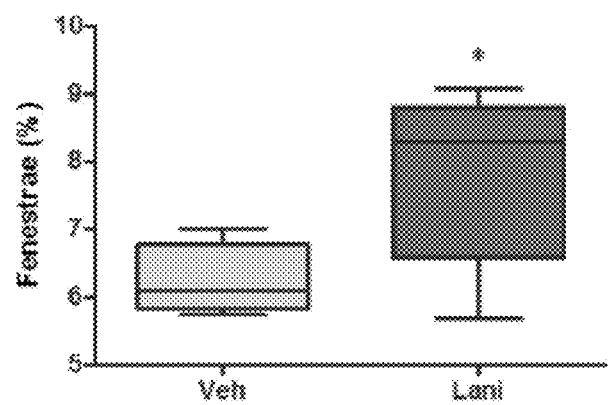

In TAA-exposed rats, lanifibranor at 100 mg/kg significantly reduced sinusoidal capillarization demonstrated by the increase in sinusoidal fenestrae (p<0.05) compared to vehicle (FIG. 4)

Von Willebrand Factor

Figure 5:
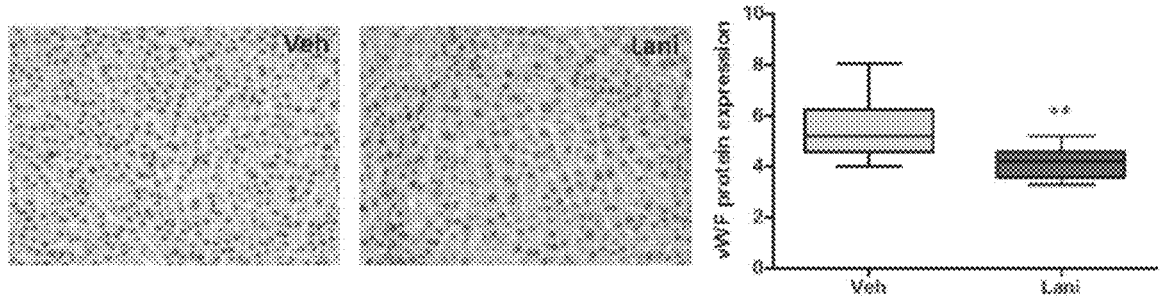
FIG. 5 shows levels of von Willebrand factor in rats treated with vehicle or lanifibranor.

In TAA-exposed rats, lanifibranor at 100 mg/kg significantly reduced the protein level of Von Willebrand factor (p<0.01) compared to vehicle (FIG. 5)

Liver Sinusoidal Endothelial Cells (LSEC)

Figure 6:
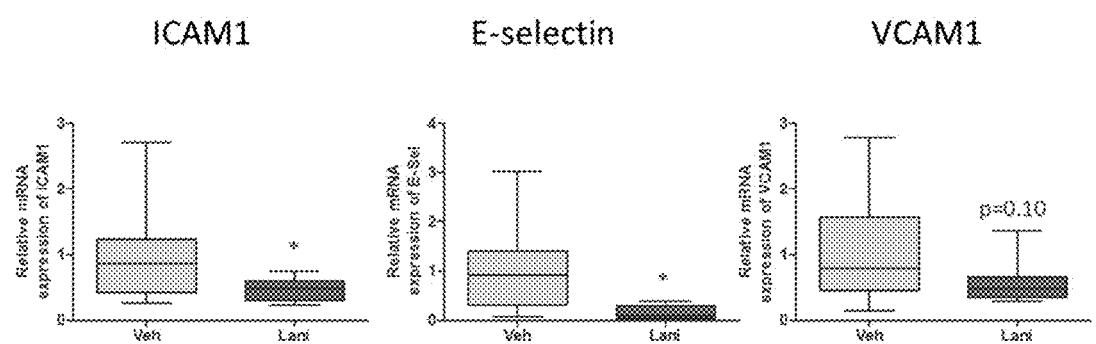
FIG. 6 shows ICAM-1, E-Selectin and VCAM-1 levels in rats treated with vehicle or lanifibranor.

In TAA-exposed rats, lanifibranor at 100 mg/kg significantly reduced LSEC activated (pro-inflammatory) phenotype demonstrated by the significant decrease in ICAM-1 and E-Selectin (P<0.05) mRNA compared to vehicle and a trend for VCAM-1 mRNA expression (FIG. 6).

IL-6 mRNA Expression

Figure 7:
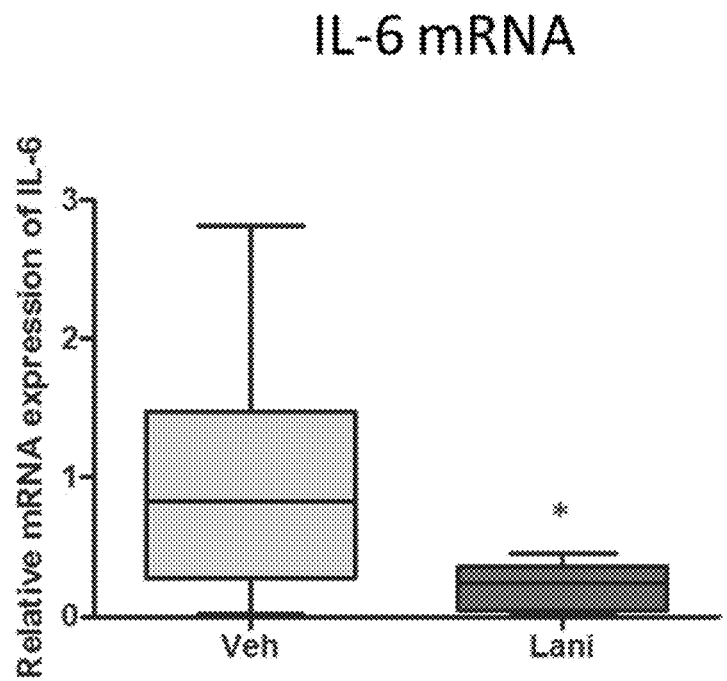
FIG. 7 shows IL-6 levels in rats treated with vehicle or lanifibranor.

In TAA-exposed rats, lanifibranor at 100 mg/kg significantly decreased IL-6 mRNA expression, a pro-inflammatory cytokine (p<0.05) compared to vehicle (FIG. 7).

AST Protein Content in Plasma

Figure 8:
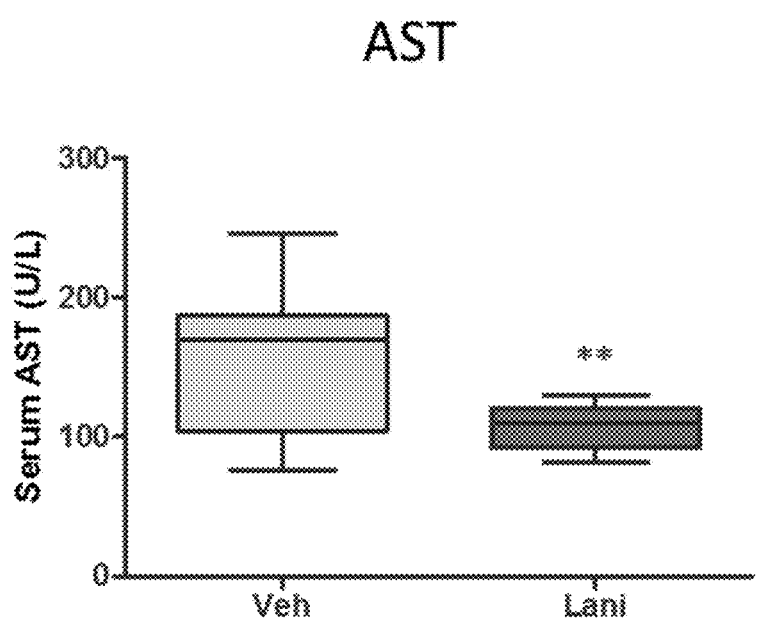
FIG. 8 shows AST levels in rats treated with vehicle or lanifibranor.

In TAA-exposed rats, lanifibranor at 100 mg/kg significantly decreased AST protein content in plasma (p<0.005) compared to vehicle (FIG. 8).

The above results show that cirrhotic rats administered with lanifibranor had significantly lower portal pressure (PP) than vehicle-treated animals with no significant changes in portal blood flow (PBF), thus indicating improved hepatic vascular resistance (HVR). In accordance with improved portal hypertension, ascites were absent in most animals treated with lanifibranor. No effects in systemic hemodynamics were observed. In addition, lanifibranor-treated rats showed significant fibrosis regression, inhibition of Hepatic Stellate cells (HSCs) activation, decrease of sinusoidal capillarization as well as improvement of liver inflammation and condition (AST). It is also worth noting that the inflammatory component of cirrhosis (expressed by IL-6 ARN levels) was significantly inhibited upon administration of lanifibranor.

Without wishing to be bound by theory, it is believed that the fact that lanifibranor displays a well-balanced activation of PPARα and PPARδ, and a partial activation of PPARγ, accounts for the results obtained, notably the decrease in sinusoidal capillarization. To the Applicant's knowledge, such an effect on sinusoidal capillarization has not been reported thus far for PPAR agonists.

REFERENCES

1. D'Amigo G, Morabito A, D'amigo M, Mlizia G, Rebora P, Valsecchi M G. Clinical states of cirrhosis. Journal of Hepatology 2018; 68:563-576
2. Martinez-Esparza M, Tristin-Manzano M, Ruiz-Alcaraz A J, García-Peñarrubia P. Inflammatory status in human hepatic cirrhosis. World J Gastroenterol. 2015; 21(41): 11522-11541
3. Dirchwolf M, Ruf A E. Role of systemic inflammation in cirrhosis: From pathogenesis to prognosis. World J Hepatol. 2015; 7(16): 1974-1981
4. Zhou W C, Zhang Q B, Qiao L. Pathogenesis of liver cirrhosis. World Journal of gastroenterology 2014; 20:7312-7324
5. Poisson J et al. Journal of Hepatology 2017, 66, 212-227
6. Turco L and Garcia-Tsao G; Clin Liver Dis, 2019, 23, 573-587
7. Lefebvre P, Chinetti G, Fruchart J C, Staels B. Sorting out the roles of PPAR alpha in energy metabolism and vascular homeostasis. J Clin Invest 2006; 116:571-580
8. Zambon A, Gervois P, Pauletto P, Fruchart J C, Staels B. Modulation of hepatic inflammatory risk markers of cardiovascular diseases by PPAR-alpha activators: clinical and experimental evidence. Arterioscler Thromb Vasc Biol 2006; 26:977-986
9. Lee C H, Olson P, Hevener A, Mehl I, Chong L-W, Olefsky J M, et al. PPARdelta regulates glucose metabolism and insulin sensitivity. Proc Natl Acad Sci USA 2006; 103:3444-3449
10. Adhikary T, Wortmann A, Schumann T, Finkernagel F, Lieber S, Roth K, Toth P M, Diederich W E, Nist A, Stiewe T, Kleinesudeik L, Reinartz S, Müller-Brüsselbach S, Müller R. The transcriptional PPARβ/δ network in human macrophages defines a unique agonist-induced activation state. Nucleic Acids Res. 2015 May 26; 43(10): 5033-5051
11. Grygiel-Gorniak B. Peroxisome proliferator-activated receptors and their ligands: nutritional and clinical implications—a review. Nutr J 2014; 13:17
12. Hazra S, Xiong S, Wang J, Rippe R A, Krishna V, Chatterjee K, et al. Peroxisome proliferator-activated receptor gamma induces a phenotypic switch from activated to quiescent hepatic stellate cells. J Biol Chem 2004; 279:11392-11401
13. Marra F, Efsen E, Romanelli R G, Caligiuri A, Pastacaldi S, Batignani G, et al. Ligands of peroxisome proliferator-activated receptor gamma modulate profibrogenic and proinflammatory actions in hepatic stellate cells. Gastroenterology 2000; 119:466-478
14. Tsai H C, Li T H, Huang C C, Huang S F, Liu R S, Yang Y Y et al. Beneficial effect of the Peroxisome proliferator-activated receptor α/γ agonist aleglitazar on progressive hepatic and splanchnic abnormalities in cirrhotic rats with portal hypertension. The Am J of Pathology 2018; 188: 1608-1624
15. Liu Y, J K, Zuo X, Jaoude J, Wei D, Shureiqi I, The Role of PPAR-δ in Metabolism, Inflammation, and Cancer Many Characters of a Critical Transcription Factor. Int J Mol Sci. 2018; 19: 3339

The invention claimed is:

1. A method of treating a cirrhotic subject at risk of progressing from compensated stage to decompensated stage, which comprises administering to the subject an effective amount of lanifibranor or of a deuterated derivative thereof, or a pharmaceutically acceptable salt thereof, or a pharmaceutically acceptable solvate thereof, whereby portal hypertension is decreased in the subject.

2. The method of claim 1, wherein the deuterated derivative of lanifibranor is a compound of formula (I):

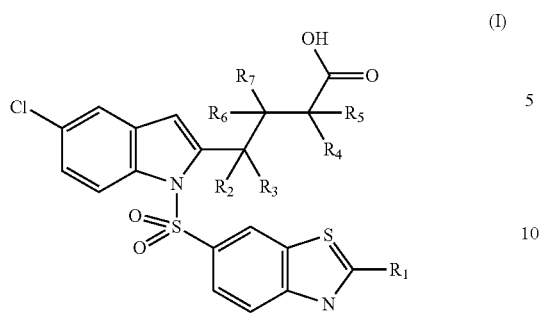

(I)

wherein at least one of the groups $R_1$ to $R_7$ is a deuterium atom and the other groups $R_1$ to $R_7$ are hydrogen atoms.

3. The method of claim 2, wherein the deuterated derivative of lanifibranor is 4-(1-(2-deuterio-1,3-benzothiazol-6-yl)sulfonyl)-5-chloro-1H -indol-2-yl)butanoic acid.

4. The method of claim 2, wherein the deuterated derivative of lanifibranor is 4-[1-(1,3-benzothiazol-6ylsulfonyl)-5-chloro-indol-2yl]-2,2,3,3,4,4-hexadeuteriobutanoic acid.

5. The method of claim 1, wherein lanifibranor is administered as a pharmaceutical composition comprising at least one pharmaceutically acceptable excipient.

6. The method of claim 5, wherein the pharmaceutical composition is a tablet.

7. The method of claim 6, wherein the tablet comprises from 100 mg to 1000 mg of lanifibranor or of a deuterated derivative thereof, pharmaceutically acceptable salt thereof, or pharmaceutically acceptable solvate thereof.

* * * * *